(12) United States Patent
Bäther et al.

(10) Patent No.: US 6,376,254 B1
(45) Date of Patent: Apr. 23, 2002

(54) BIOMIMETIC REAGENT SYSTEM AND ITS USE

(75) Inventors: Wolfgang Bäther, Lübeck; Hans-Jürgen Duchstein, Pinneberg; Susanne Hoffmann, Buchholz, all of (DE)

(73) Assignee: Dräger Sicherheitstechnik GmbH (DE)

( * ) Notice: Subject to any disclaimer, the term of this patent is extended or adjusted under 35 U.S.C. 154(b) by 0 days.

(21) Appl. No.: 09/394,969

(22) Filed: Sep. 10, 1999

(30) Foreign Application Priority Data

Mar. 19, 1999 (DE) .......................... 199 12 380

(51) Int. Cl.[7] .............................. G01N 21/78
(52) U.S. Cl. .................. 436/140; 436/167; 422/86; 422/88
(58) Field of Search ................ 436/140, 164, 436/167, 169, 181; 422/55, 86, 87, 88, 91

(56) References Cited

U.S. PATENT DOCUMENTS 4,864,041 A * 9/1989 Hill
5,063,164 A * 11/1991 Goldstein
5,516,636 A * 5/1996 McCapra
5,712,402 A * 1/1998 Pinnavaia et al.
6,020,288 A * 2/2000 Nonomura et al.
6,028,025 A * 2/2000 Ying et al.
6,103,892 A * 8/2000 Breslow et al.

FOREIGN PATENT DOCUMENTS

DE 3407 686 C1 7/1985
DE 39 02 402 C1 6/1990

OTHER PUBLICATIONS

A.M. Gonsalves et al "State of the Art in the Development of Biomimetic Oxidation Catalysts" Jourman of Molecular Catalysis A: Chemical, Vol. 113 (1996), pp. 209–211.*

* cited by examiner

Primary Examiner—Jeffrey Snay
(74) Attorney, Agent, or Firm—McGlew and Tuttle, P.C.

(57) ABSTRACT

A biomimetic reagent system is provided containing an oxygen donor and a catalyst based on porphyrin, which are applied to a carrier. A device that contains the system is also provided for determining components of gas or vapor samples, especially aromatics, such as benzene. A process for hydroxylating aromatics, such as benzene, using the biomimetic reagent system is also provided.

30 Claims, 1 Drawing Sheet

Detector tube: biomimetic reagent system

Detector tube: biomimetic reagent system
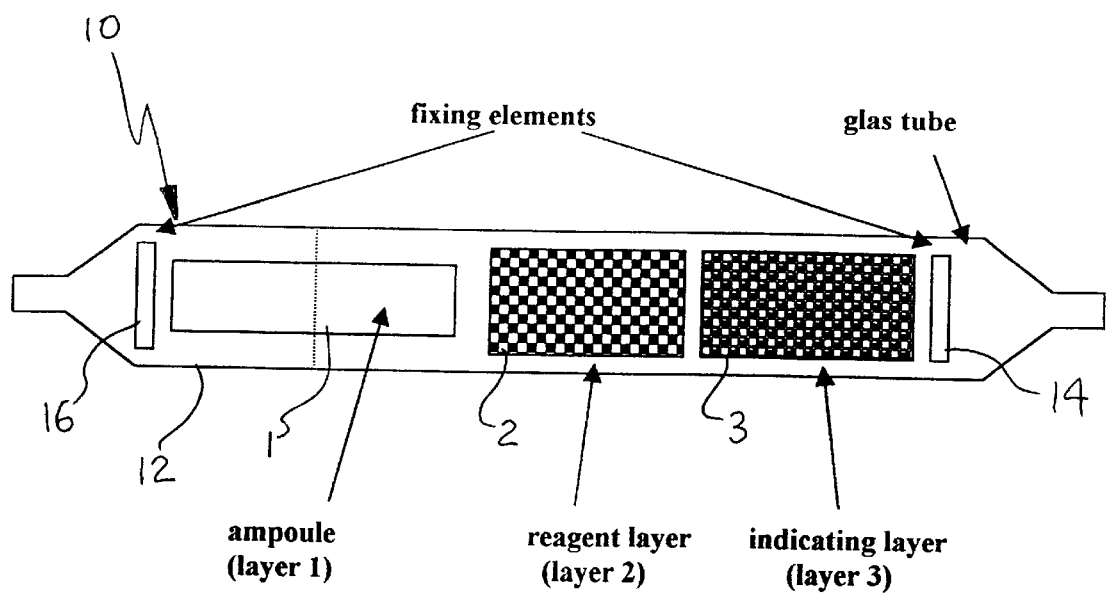

BIOMIMETIC REAGENT SYSTEM AND ITS USE

FIELD OF THE INVENTION

The present invention pertains to a biomimetic reagent system, which is applied to a carrier and contains an oxygen donor and a catalyst based on porphyrin, to a device containing this reagent system, to its use for determining components of gas or vapor samples, especially aromatics, such as benzene, as well as to a process for hydroxylating aromatics, such as benzene, by using the biomimetic reagent system.

BACKGROUND OF THE INVENTION

Various embodiments of testing elements with reagent systems, by means of which especially gases or vapors can be tested for components contained in them in a simple manner, rapidly and at low cost, have been known.

A measuring apparatus operating with a reagent-containing indicator strip is described in DE 34 07 686 C1. The gas to be tested is drawn actively through this indicator strip. The reagents on the indicator strip react specifically with the components to be determined in the sample. This leads to a change in color, which is detected photometrically.

Another embodiment is a plaque. A flat disk, e.g., a paper disk, which is impregnated with a reagent, reacts with the components of the gas sample to be determined, e.g., air, based on diffusion, while the color of the disk changes. The intensity of the change in color within a certain period of time is an indicator of the concentration of the constituents of the air.

The testing elements are also often designed as so-called detector tubes. The reagents in these are applied, in general, as very thin layers to fine-grained carrier materials, which are in turn fixed in a glass tube. The gas sample (analyte) is then actively drawn through the glass tube by means of a pump. The components to be determined now react with the reagents, while the color changes. The length of the color layer formed relative to a defined sample volume is an indicator of the concentration of the component to be determined. A plurality of layers of different chemical reactivity, which are arranged one behind the other, may be used within the same tube. For example, the analyte can be converted in a preceding layer into a chemically different analyte, for the detection of which there will be a suitable color reaction in another layer.

The automatic optoelectronic evaluation of the corresponding change in color of miniaturized detector tubes is usually performed as described in DE 39 02 402 C1.

A great variety of chemical reagent systems, which must meet a great variety of requirements, are used precisely in detector tubes. Besides the redox reagent systems, which are used very frequently, the changes in the pH value or even condensation reactions also play an important role in the systems used. Since the reactions of the reagent systems usually must take place as completely as possible at room temperature and within a very short time, the reagent matrices are, in general, chemically highly corrosive; for example, redox reactions take place with the use of fuming sulfuric acid. The gases released during an active operation, e.g., sulfur trioxide in this case, may cause damage, especially in automated measuring systems. Such corrosive reagent systems consequently have limited suitability for use in automated measuring systems. Furthermore, an accurate and complicated coordination of the properties of the reagent system and the carrier material used must be usually performed.

Moreover, the use of biochemical reagent systems in detector tubes has been known. Even though these highly complex systems are characterized by a high selectivity, their limited shelf life is disadvantageous.

Testing elements in the form of so-called biomimetic sensors have been known from the state of the art as well. Biomimetic sensors simulate the function of organs of sense: Chemical signals are recoded into physical signals or also vice versa by influencing the interaction between the carrier and bioactive materials. The response of the biomimetic sensor to such signals simulates the response of an organ of sense. The physicochemical signals are then converted by means of so-called transducers into measurable electric signals and optionally suitably amplified by an electronic component.

A biomimetic sensor system for determining the concentration of CO and other pollutants in air has been known from U.S. Pat. No. 5,063,164. The sensor reacts to the presence of CO with a sensitivity similar to that of the human organs of sense, i.e., it simulates the response of the human body to the presence of CO, etc. The sensor disclosed in U.S. Pat. No. 5,063,164 has a good service life. However, it consists of a very complex reagent system, which comprises five groups of inorganic/organic reagents, and some of the inorganic reagents are enclosed in larger organic molecules and these are in turn introduced into the pores of suitable carriers. The biomimetic sensor known from U.S. Pat. No. 5,063,164 also has the drawback that organic materials are made accessible for detection only by preceding reaction steps, such as oxidation by corrosive oxidizing agents into CO or by reactions induced by increasing the temperature.

SUMMARY AND OBJECTS OF THE INVENTION

Thus, the object of the present invention is to provide a biomimetic reagent system, which is suitable for the determination of components of gas or vapor samples, especially for determining organic materials of high toxicity, such as benzene. The biomimetic reagent system should be characterized by mild reaction conditions, i.e., it shall be able to be used at room temperature and without additional chemically corrosive auxiliary reagents and have a service life sufficient for practical purposes. Another object of the present invention was to provide a gas sensor that contains the biomimetic reagent system.

According to the invention, a biomimetic reagent system is provided that includes an oxygen donor and a catalyst based on porphyrin which are applied to a carrier.

The present invention also pertains to the use of the reagent system according to the present invention for determining components, especially aromatics, such as benzene, in gas and vapor samples.

The present invention also pertains to a process for hydroxylating aromatics by using the reagent system according to the present invention.

The present invention also pertains to a device containing the reagent system according to the present invention.

As was described above, biomimetic reagent systems are chemical models for one or more biochemical reactions. In the present invention, they are metal complexes, which are able to imitate, as a biomimetic system, monooxygenase reactions that are catalyzed by cytochrome P-450. Monooxygenases are enzymes that are able to activate oxygen by taking up two electrons and two protons and to hydrolyze or epoxidize substrates as a result. These reactions, which take place in the human body, are indispensable for the human body for the detoxification of drugs and foreign substances and after metabolism in the liver, they usually lead to water-soluble compounds, which are excreted renally.

These reactions are oxygenation reactions, in which the oxygen must be reduced enzymatically by NADPH. However, these reductions are difficult to carry out in the model with oxygen as the oxidizing agent.

It was surprisingly found according to the present invention that by using a carrier-bound biomimetic system, which contains certain oxygen donors combined with catalysts based on porphyrin, it is possible to react aromatics, especially benzene, into 1,4-benzoquinone derivatives under mild conditions, and these derivatives can then be easily made visible in color by condensation with 2,4-dinitrophenylhydrazine into the hydrazone.

This is surprising especially because molecules of low reactivity, such as benzene, which is highly resistant especially to oxidation, do not normally react chemically under such mild conditions, especially at a solid-gas interface.

The oxygen donor in the reagent system according to the present invention is selected from the group comprising iodosobenzene, magnesium monoperoxyphthalate, cumene hydroperoxide, hydrogen peroxide, hypochlorite, especially sodium hypochlorite, amine N-oxide, inorganic persulfate and mixtures thereof The oxygen donor contains, in particular, iodosobenzene, and the oxygen donor is preferably iodosobenzene. The said compounds per se and their preparation have been known from the state of the art.

The catalyst component of the reagent system according to the present invention contains, in general, a metalloporphyrin derivative, especially a substituted metalloporphyrin. The catalyst contains, e.g., a metal salene (salene is an abbreviation for N,N'-bis(salicylidene)-ethylenediimino) (N,N'-bis(salicylidene)-ethylenediimino-cobalt (II)), a tetraphenylporphyrin skeleton with iron or manganese, especially iron(III) tetraphenylporphyrin or manganese(III) tetraphenylporphyrin, preferably 5,10,15,20-tetrakis(pentafluoro)phenylporphyrin-Fe(III)Cl (FeTFPPCl), 5,10,15,20-tetrakis(2,6-dichlorophenyl)porphyrin-Fe(III)Cl (FeTDCPP) and/or octabromo-5,10,15,20-tetrakis(2,6-dichlorophenyl)porphyrin-Fe(III)Cl (FeOBTDCPP). FeTFPPCl is a synthetic metalloporphyrin with halogen substituents on the phenyl rings of the porphyrin skeleton. Its preparation, like that of the other porphyrin derivatives mentioned, is known to the person skilled in the art.

The suitable carrier materials of the reagent system according to the present invention are solids, such as silica gel, quartz glass or glass grains, silica gel being preferably used.

The particle size of the carrier materials is, in general, not critical. Fine-grained carrier material with a particle diameter small than 1 mm, especially smaller than 0.5 mm, and preferably smaller than 0.5 mm and larger than 0.2 mm is used, in general.

The components described so far are used, in general, at an oxygen donor: catalyst: carrier ratio of $10^{-2}$ to $10^{-3}$ moles: $10^{-5}$ to $10^{-6}$ moles: 0.5 to 1.0 g and especially at $5 \times 10^{-3}$ moles: $5 \times 10^{-6}$: 0.7 to 0.8 g.

A biomimetic reagent system that is composed of iodosobenzene and 5,10,15,20-tetrakis(pentafluoro)phenylporphyrin-Fe(III)Cl on fine-grained silica gel is particularly preferred.

A suitable reagent system for detecting, e.g., benzene is thus composed, e.g., of 80 g of silica gel carrier, 0.5 g of FeTFPPCl and 10 g of iodosobenzene.

The reagent system according to the present invention is prepared, in general, by intimately mixing the components with one another. For better adsorption on the carrier, the reagent system is usually first moistened with a solvent, such as dichloromethane, and is then mixed with the carrier material, e.g., silica gel. The solvent is then allowed to evaporate.

Using such a reagent system according to the present invention, it is possible to react, e.g., benzene into 1,4-benzoquinone under mild conditions, i.e., at room temperature and without additional auxiliary reagents. The stability and consequently the catalytic activity are obviously influenced especially advantageously by steric and electronic effects of the substituents of the porphyrins according to the present invention, especially FeTFPPCl. The sterically shielded complexes are highly resistant to oxidation and therefore stable for a long time.

Without being bound to a certain theory, it is assumed that the cause of this is a special reaction mechanism, which is determined by the reagent system according to the present invention. For example, a metal-oxo complex formed from an oxygen donor and metalloporphyrin attacks the aromatic compound such that a substituted 1,4-cyclohexadienyl radical is formed, which is converted by a second attack of the metal-oxo complex into a cyclohexadiene derivative. A hydroquinone is formed from this by splitting off the metalloporphyrin. The hydroquinone can then be reacted very rapidly into quinone under the reaction conditions and into the hydrazone by condensation with 2,4-dinitrophenylhydrazine.

The above reactions take place, in general, at temperatures of 10° C. to 40° C. and under pressures of 700 to 1,300 hPa.

Thus, the reagent system according to the present invention offers a process for hydroxylating aromatics, especially benzene.

As was described above, the reagent system according to the present invention reacts biomimetically to the presence of aromatics, such as benzene. The benzoquinone formed in the above-described reaction can then be made visible, e.g., by complex formation with hydroquinone (bluish green color). The coupling reaction with 2,4-dinitrophenylhydrazine, which leads to a red color with concentrated sulfuric acid (hydrazone formation), is another suitable detection reaction.

Thus, the reagent system according to the present invention can be used to detect or determine aromatics, e.g., benzene, as a component of gas or vapor samples. Very small amounts in the lower ppm range can be quantitatively detected. Consequently, the sensitivity of the reagent system according to the present invention to the presence of benzene is similar to that of the human body. In addition, it has a very good service life of more than 1 year for practical application.

Thus, the biomimetic reagent system according to the present invention may also be used in devices that are suitable for determining components of gas or vapor samples, e.g., as a gas-measuring system.

For example, the biomimetic reagent system according to the present invention may be arranged in a detector tube, which is then used for quantitative gas analysis in conjunction with pumps to be operated manually or automatically.

For use for measurement, the tips of the detector tubes, which were previously sealed in a gas-tight manner, are broken off, the detector tube is introduced into a corresponding gas-detecting pump and the specified volume of gas or vapor is drawn through the reaction layer by means of the pump. Most detector tubes are so-called scaled tubes, in which the color of the indication layer changes over a length that depends on the analyte concentration. Furthermore, detector tubes with a color comparison layer have been known, by means of which a color comparison is performed after the reaction. Contrary to this, so-called collection tubes contain coconut shell carbon, various types of silica gel or molecular sieves. Because of their exclusive collection behavior without a color change, these tubes can also be described as detector tubes without direct display, which are subsequently evaluated by an analytical determination method (e.g., HPLC: High Pressure Liquid Chromatography, GC: Gas Chromatography, GC-MS: GC-Mass Spectrometry) (Dräger-Röhrchen Handbuch [Dräger Tube Manual], 1994).

One embodiment of the present invention may be such that the analyte, e.g., benzene, is chemically reacted, e.g., oxidized into benzoquinone in the case of benzene, in a reagent layer, and then transported by means of an extracting agent into a next layer, in which a detection reagent (e.g., 2,4-dinitrophenylhydrazine) is present. The intensity of the color formed in this second layer is now an indicator of the concentration of the analyte. It is also conceivable to bind the indicator of the second layer covalently to the carrier by strong adsorption forces and to thus form a scaled tube with a liquid transporting agent (extracting agent).

A measuring system based on the detection reagent 2,4-dinitrophenylhydrazine is particularly advantageous.

Finally, there are also embodiments in which volatile oxidation products are produced (e.g., oxidation of methane into formaldehyde, methanol, formic acid or CO). These products do not need to be transported into the second layer with an extracting agent, but they reach that layer with the gas flow and can then be displayed in a scaled tube.

Thus, the present invention also provides a device that contains the biomimetic reagent system, and is suitable for the determination of components of gas or vapor samples.

The present invention will be explained on the basis of exemplary embodiments below.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

In the drawings:

The only FIGURE is a side view of a detector tube used with the reagent system according to the invention.

DESCRIPTION OF THE PREFERRED EMBODIMENTS

Referring to the drawing in particular, the invention comprises a biomimetic reagent system, which uses a detector tube generally designated 10. The detector tube 10 per includes a glass tube 12 which defines an interior. Fixing elements 14 and 16 are provided in the interior of glass tube 12, to each side of the three layers 1,2 and 3. Layer 1 is an ampule, layer 2 is a reagent layer and layer 3 is an indicating layer.

EXAMPLE 1

Preparation of the Biomimetic Reagent System

Forty g of silica gel were mixed intensely with 10 g of iodosobenzene and 0.3 mL of water for 10 minutes at room temperature. Separately from this, 40 g of silica gel, 0.5 g of catalyst and 0.5 mL of dichloromethane were mixed for 10 minutes at room temperature. These two mixtures were subsequently mixed together intensely for 30 minutes, likewise at room temperature.

EXAMPLE 2

Determination of Benzene

The reagent system prepared in Example 1 was introduced into a conventional Dräger tube (detector tube). The detector tube comprised three layers 1,2 and 3:
1. An ampule, which was filled with an ethanol-water mixture (30/70 vol. %) as a liquid extracting agent,
2. a reagent matrix, which consisted of the carrier material prepared in Example 1, and
3. an indicator layer, which contained 2,4-dinitrophenylhydrazine as the reagent.

The detector tube containing the three layers was closed at both of its ends. To determine benzene, the two ends of the detector tube were broken off and the benzene-containing air was drawn through the tube by means of a pump. The benzene collected on layer 2 and was reacted into benzoquinone in the biomimetic reaction. The ampule with the extracting agent was then broken open and the extracting liquid was thus released. Using the pump, the liquid was then drawn through the layer 2, while the benzoquinone dissolved in the extracting agent and thus entered layer 3 (indication layer). The benzoquinone formed was made visible there with the indicator 2,4-dinitrophenylhydrazine in the form of an orange yellow color.

The FIGURE shows a detector tube comprised of the three layers: 1. An ampule, which was filled with an ethanol-water mixture (30/70 vol. %) as a liquid extracting agent, 2 a reagent matrix, which consisted of the carrier material prepared in Example 1, and 3. an indicator layer, which contained 2,4-dinitrophenylhydrazine as the reagent.

In examples 1 and 2 for the reagent system the oxygen donor iodosobenzene may be replaced with magnesium monoperoxyphthalate, cumene hydroperoxide, hydrogen peroxide, hypochlorite, amine N-oxide, inorganic persulfate, and mixtures thereof. Thehypochloritemay be sodium hypochlorite. The catalyst may be provided containing metalloporphyrin, substituted metalloporphyrin, metal salenes, a substituted tetraphenylporphyrin skeleton with iron or manganese, iron(III) tetraphenylporphyrin or manganese(III) tetraphenylporphyrin. Advantageously, the catalyst is 5,10,15,20-tetrakis(pentafluoro)phenylporphyrin-Fe(III)Cl. The carrier material may contain silica gel in each embodiment wherein the carrier material is a fine-grained material with a particle diameter smaller than 1 mm, especially smaller than 0.5 mm and preferably smaller than 0.5 mm and larger than 0.2 mm. Advantageously, the reagent system contains iodosobenzene and 5,10,15,20-tetrakis (pentafluoro)phenylporphyrin-Fe(III)Cl on silica gel. The oxygen donor: catalyst: carrier ratio is $10^{-2}$ to $10^{-3}$ moles:$10^{-5}$ to $10^{-6}$ moles:0.5 to 1.0 g and especially $5 \times 10^{-3}$ moles:$5 \times 10^{-6}$ moles:0.7 to 0.8 g.

While specific embodiments of the invention have been described in detail to illustrate the application of the principles of the invention, it will be understood that the invention may be embodied otherwise without departing from such principles.

What is claimed is:

1. Biomimetic reagent system for detecting the presence of an aromatic component in a gas or vapor sample, which comprises a carrier, a metalloporphyrin catalyst, an oxygen donor for oxidizing such an aromatic component in the presence of the catalyst, the catalyst and the oxygen donor being applied to the carrier, and an indicator reagent for indicating such an oxidized aromatic component in the gas or vapor sample, wherein the ratio of oxygen donor:catalyst:carrier is from $10^{-2}$ to $10^{-3}$ moles oxygen donor:from $10^{-5}$ to $10^{-6}$ moles catalyst:from 0.5 to 1.0 g carrier.

2. System of claim 1 wherein the oxygen donor is selected from the group consisting of iodosobenzene, magnesium monoperoxy phthalate, cumene hydroperoxide, hydrogen peroxide, hypochlorite, amine N-oxide, inorganic persulfate, and mixtures thereof.

3. System of claim 2 wherein the hypochlorite is sodium hypochlorite.

4. System of claim 1 wherein the catalyst comprises a member selected from the group consisting of metalloporphyrin, substituted metalloporphyrin, and metal salene.

5. System of claim 1 wherein the catalyst comprises metalloporphyrin.

6. System of claim 1 wherein the catalyst comprises substituted metalloporphyrin.

7. System of claim 1 wherein the catalyst comprises a metal salene.

8. System of claim 1 wherein the catalyst comprises a substituted tetraphenyl porphyrin skeleton with iron or manganese.

9. System of claim 1 wherein the catalyst comprises iron (III) tetraphenyl porphyrin or manganese (III) tetraphenyl porphyrin.

10. System of claim 1 wherein the catalyst comprises 5,10,15,20-tetrakis (pentafluoro) phenyl porphyrin—Fe (III) Cl.

11. System of claim 1 wherein the carrier comprises silica gel.

12. System of claim 1 wherein the carrier comprises fine grain material having a particle diameter smaller than 1 mm.

13. System of claim 1 wherein the carrier comprises fine grain material having a particle diameter smaller than 0.5 mm.

14. System of claim 1 wherein the carrier comprises fine grain material having a particle diameter smaller than 0.5 and larger than 0.2 mm.

15. System of claim 1 wherein the carrier comprises silica gel, the oxygen donor comprises iodosobenzene and the catalyst comprises 5,10,15,20-tetrakis (pentafluoro) phenyl porphyrin—Fe (III) Cl, the iodosobenzene and 5,10,15,20-tetrakis (pentafluoro) phenyl porphyrin—Fe (III) Cl being applied to the silica gel.

16. System of claim 1 wherein the ratio of oxygen donor:catalyst:carrier is $5 \times 10^{-3}$ moles oxygen donor:$10^{-6}$ moles catalyst:0.7 to 0.8 g carrier.

17. System of claim 1 wherein the indicator reagent is 2,4-dinitrophenyl hydrazine.

18. Biomimetic reagent system for detecting the presence of an aromatic component in a gas or vapor sample, which comprises a carrier, a metalloporphyrin catalyst, an oxygen donor for oxidizing such an aromatic component in the presence of the catalyst, the catalyst and the oxygen donor being applied to the carrier, and an indicator reagent for indicating such an oxidized aromatic component in the gas or vapor sample, wherein the oxygen donor is selected from the group consisting of iodosobenzene, magnesium monoperoxy phthalate, cumene hydroperoxide, hydrogen peroxide, hypochlorite, amine N-oxide, inorganic persulfate, and mixtures thereof, and wherein the catalyst comprises a member selected from the group consisting of metalloporphyrin, substituted metalloporphyrin, and metal salene.

19. System of claim 18 wherein the ratio of oxygen donor:catalyst:carrier is from $10^{-2}$ to $10^{-3}$ moles oxygen donor:from $10^{-5}$ to $10^{-6}$ moles catalyst:from 0.5 to 1.0 g carrier.

20. System of claim 18 wherein the carrier comprises silica gel.

21. System of claim 18 wherein the indicator reagent is 2,4-dinitrophenyl hydrazine.

22. Method of using the biomimetic reagent system of claim 1 for detecting the presence of an aromatic component in a gas or vapor sample, comprising contacting such gas or vapor sample with the carrier onto which the catalyst and oxygen donor are applied for oxidizing such an aromatic component by the oxygen donor in the presence of the catalyst, and contacting the resulting oxidized aromatic component with the indicator reagent for indicating the presence of such aromatic component in the gas or vapor sample.

23. Method of claim 22 wherein the oxygen donor is selected from the group consisting of iodosobenzene, magnesium monoperoxy phthalate, cumene hydroperoxide, hydrogen peroxide, hypochlorite, amine N-oxide, inorganic persulfate, and mixtures thereof, and the catalyst comprises a member selected from the group consisting of metalloporphyrin, substituted metalloporphyrin, and metal salene.

24. Method of claim 22 wherein the indicator reagent is 2,4-dinitrophenyl hydrazine.

25. Method of claim 22 wherein the aromatic component being detected is benzene.

26. Method of claim 22 wherein the reagent system is disposed in a detector tube, and the gas or vapor sample is conducted through the tube for contact with the carrier onto which the catalyst and oxygen donor are applied, and in turn for contact of the resulting oxidized aromatic component with the indicator reagent.

27. Device comprising a container containing a biomimetic reagent system for detecting the presence of an aromatic component in a gas or vapor sample, the reagent system comprising a carrier, a metalloporphyrin catalyst, an oxygen donor for oxidizing such an aromatic component in the presence of the catalyst, the catalyst and the oxygen donor being applied to the carrier, and an indicator reagent for indicating such an oxidized aromatic component in the gas or vapor sample, wherein the ratio of oxygen donor:catalyst:carrier is from $10^{-2}$ to $10^{-3}$ moles oxygen donor:from $10^{-5}$ to $10^{-6}$ moles catalyst:from 0.5 to 1.0 g carrier.

28. Device of claim 27 wherein the oxygen donor is selected from the group consisting of iodosobenzene, magnesium monoperoxy phthalate, cumene hydroperoxide, hydrogen peroxide, hypochlorite, amine N-oxide, inorganic persulfate, and mixtures thereof, and the catalyst comprises a member selected from the group consisting of metalloporphyrin, substituted metalloporphyrin, and metal salene.

29. Device of claim 27 wherein the indicator reagent is 2,4-dinitrophenyl hydrazine.

30. Device of claim 27 wherein the container comprises a detector tube in which the reagent system is disposed.

* * * * *